(12) United States Patent
Schilffarth et al.

(10) Patent No.: US 9,810,707 B2
(45) Date of Patent: Nov. 7, 2017

(54) CHIP-BASED FLOW CYTOMETER TYPE SYSTEMS FOR ANALYZING FLUORESCENTLY TAGGED PARTICLES

(75) Inventors: Adam Richard Schilffarth, Austin, TX (US); William R. Deicher, Austin, TX (US); John C. Carrano, Austin, TX (US); Jesse C. Phillips, Austin, TX (US)

(73) Assignee: LUMINEX CORPORATION, Austin, TX (US)

( * ) Notice: Subject to any disclaimer, the term of this patent is extended or adjusted under 35 U.S.C. 154(b) by 1926 days.

(21) Appl. No.: 11/750,000

(22) Filed: May 17, 2007

(65) Prior Publication Data

US 2007/0269345 A1 Nov. 22, 2007

Related U.S. Application Data

(60) Provisional application No. 60/747,483, filed on May 17, 2006.

(51) Int. Cl.
| | |
|---|---|
| *G01N 33/00* | (2006.01) |
| *G01N 35/10* | (2006.01) |
| *G01N 35/00* | (2006.01) |
| *G01N 15/14* | (2006.01) |
| *G01N 21/64* | (2006.01) |

(52) U.S. Cl.
CPC ..... *G01N 35/1095* (2013.01); *G01N 15/1484* (2013.01); *G01N 35/0098* (2013.01); *G01N 15/1459* (2013.01); *G01N 2021/6439* (2013.01)

(58) Field of Classification Search
CPC ............... G01N 15/14; G01N 35/1095; G01N 15/1484; G01N 35/0098; G01N 15/1459; G01N 2021/6439

USPC ......................................... 422/73; 435/289.1
See application file for complete search history.

(56) References Cited

U.S. PATENT DOCUMENTS

| | | | |
|---|---|---|---|
| 5,736,330 A | 4/1998 | Fulton | |
| 5,760,900 A | 6/1998 | Ito et al. | |
| 5,780,857 A * | 7/1998 | Harju et al. | ............... 250/458.1 |

(Continued)

FOREIGN PATENT DOCUMENTS

| | | |
|---|---|---|
| EP | 1754964 | 2/2007 |
| WO | 01/27590 | 4/2001 |

(Continued)

OTHER PUBLICATIONS

De La Fuente et al., "A SU-8 Microfluidic Total Analysis System integrating silicon photodiodes and buried waveguides," Proceedings of Spanish Conference on Electron Devices, 2005, pp. 461-464.

(Continued)

*Primary Examiner* — William H Beisner
*Assistant Examiner* — Liban Hassan
(74) *Attorney, Agent, or Firm* — Parker Highlander PLLC

(57) ABSTRACT

Portable systems for processing and analyzing biological or environmental samples as well as different configurations of chip-based flow cytometers are provided. The portable systems include an automated assay preparation module configured to process a sample into a fluid assay with fluorescently tagged particles and a microfluidic analysis module coupled to the fluid assay module, wherein the microfluidic analysis module includes a chip-based flow cytometer.

19 Claims, 10 Drawing Sheets

(56) References Cited

U.S. PATENT DOCUMENTS

| | | | |
|---|---|---|---|
| 5,981,180 | A | 11/1999 | Chandler et al. |
| 6,057,107 | A | 5/2000 | Fulton |
| 6,159,739 | A | 12/2000 | Weigl et al. |
| 6,268,222 | B1 | 7/2001 | Chandler et al. |
| 6,403,367 | B1 | 6/2002 | Cheng et al. |
| 6,449,562 | B1 | 9/2002 | Chandler et al. |
| 6,506,609 | B1 | 1/2003 | Wada et al. |
| 6,514,295 | B1 | 2/2003 | Chandler et al. |
| 6,524,793 | B1 | 2/2003 | Chandler et al. |
| 6,528,165 | B2 | 3/2003 | Chandler |
| 6,592,821 | B1 | 7/2003 | Wada et al. |
| 6,592,822 | B1 | 7/2003 | Chandler |
| 6,608,360 | B2 | 8/2003 | Starikov et al. |
| 6,635,487 | B1 | 10/2003 | Lee et al. |
| 6,844,563 | B2 | 1/2005 | Emoto |
| 6,875,619 | B2 | 4/2005 | Blackburn |
| 6,881,979 | B2 | 4/2005 | Starikov et al. |
| 6,906,792 | B2 | 6/2005 | Ortyn et al. |
| 7,105,355 | B2 | 9/2006 | Kurabayashi et al. |
| 7,245,379 | B2 | 7/2007 | Schwabe ............... 356/436 |
| 2002/0028519 | A1* | 3/2002 | Yguerabide et al. ......... 436/518 |
| 2003/0054558 | A1* | 3/2003 | Kurabayashi et al. ......... 436/63 |
| 2003/0142291 | A1* | 7/2003 | Padmanabhan et al. ....... 356/39 |
| 2003/0186465 | A1* | 10/2003 | Kraus et al. ................. 436/526 |
| 2004/0025950 | A1 | 2/2004 | Larsen et al. |
| 2004/0043509 | A1 | 3/2004 | Stahler et al. |
| 2004/0062468 | A1 | 4/2004 | Lee |
| 2004/0233424 | A1 | 11/2004 | Lee et al. |
| 2005/0003464 | A1* | 1/2005 | Tibbe et al. ................. 435/7.23 |
| 2005/0078299 | A1 | 4/2005 | Fritz et al. |
| 2005/0106739 | A1 | 5/2005 | Cabuz et al. |
| 2005/0157301 | A1 | 7/2005 | Chediak et al. |
| 2005/0274618 | A1 | 12/2005 | Lee et al. |
| 2006/0008227 | A1 | 1/2006 | Schmidt et al. |
| 2006/0011552 | A1 | 1/2006 | Utsunomiya |
| 2006/0234267 | A1* | 10/2006 | Besemer et al. ............... 435/6 |

FOREIGN PATENT DOCUMENTS

| | | |
|---|---|---|
| WO | 03/046511 | 6/2003 |
| WO | WO 03/054525 | 7/2003 |
| WO | 2005/083423 | 9/2005 |

OTHER PUBLICATIONS

Fu et al., "Electrokinetically driven micro flow cytometers with integrated fiber optics for on-line cell/particle detection," Analytica Chimica Acta, vol. 507, 2004, pp. 163-169.

Grumann et al., "Direct Hemoglobin Measurement by Monolithically Integrated Optical Beam Guidance," International Conference on Solid-State Sensors, Actuators & Microsystems, 2005, pp. 1106-1109.

Jorgensen et al., "A biochemical microdevice with an integrated chemiluminescence detector," Sensors & Actuators, Series B, vol. 90, 2003, pp. 15-21.

Lee et al., "Micro flow cytometers with buried SU-8/SOG optical waveguides," Sensors & Actuators, Series A, vol. 103, 2003, pp. 165-170.

Lien et al., "Monolithic photonics-microfluidics integration for micro-total analysis systems," Conference on Lasers & Electro Optics, 2003, 3 pages.

Lien et al., "Monolithically Integrating Photonic and Microfluidic Devices Using a Self-Aligned Process," IEEE LEOS Annual Meeting Conference Proceedings, 2003, vol. 2, pp. 525-526.

Lien et al., "High-Sensitivity Cytometric Detection Using Fluidic-Photonic Integrated Circuits with Array Waveguides," IEEE Journal of Selected Topics in Quantum Electronics, vol. 11, No. 4, 2005, pp. 827-834.

Misiakos et al., "A bioanalytical microsystem for protein and DNA sensing based on a monolithic silicon optoelectronic transducer," Journal of Physics, Conference Series 10, 2005, pp. 273-276.

Miyake et al., "Investigation of Sheath Flow Chambers for Flow Cytometers," JSME International Journal, Series B, vol. 40, No. 1, 1997, pp. 106-113.

Schaefer et al., "Monolithic Integrated Optical Detection for Microfluidic Systems using Thin Film Photodiodes based on Amorphous Silicon," IEEE International Conference on Micro Electro Mechanical Systems, 2005, pp. 758-761.

Seo et al., "Disposable integrated microfluidics with self-aligned planar microlenses," Sensors & Actuators, Series B, vol. 99, 2004, pp. 615-622.

Thrush et al., "Integrated semiconductor bio-fluorescence sensor integrated on micro-fluidic platform," Conference on Lasers & Electro Optics, 2004, vol. 2, 2 pages.

Tung et al., "PDMS-based opto-fluidic micro flow cytometer with two-color, multi-angle fluorescence detection capability using PIN photodiodes," Sensor & Actuators, Series B, vol. 98, 2004, pp. 356-367.

Wang et al., "Microchip Flow Cytometer with Integrated Polymer Optical Elements for Measurement of Scattered Light," IEEE International Conference on Micro Electro Mechanical Systems, 2004, pp. 367-370.

Wang et al., "Measurements of scattered light on a microchip flow cytometer with integrated polymer based optical elements," Lab Chip, vol. 4, 2004, pp. 372-377.

Wang et al., "Microchip Flow Cytometer with Integrated Polymer Optics for Fluorescence Analysis of Cells," International Conference on Miniaturized Systems for Chemistry & Life Sciences, 2004, pp. 460-462.

Wolff et al., "Integrating advanced functionality in a microfabricated high-throughput fluorescent-activated cell sorter," Lap Chip, vol. 3, 2003, pp. 22-27.

Yin et al., "Integrated biophotonic sensor with single-molecule resolution," Conference on Lasers & Electro Optics, 2004, 2 pages.
International Search Report, PCT/US2007/069147, dated Feb. 29, 2008.

* cited by examiner

CHIP-BASED FLOW CYTOMETER TYPE SYSTEMS FOR ANALYZING FLUORESCENTLY TAGGED PARTICLES

BACKGROUND OF THE INVENTION

1. Field of the Invention

The present invention generally relates to systems for processing and analyzing fluid samples. Certain embodiments relate to chip based flow cytometer type systems configured to perform measurements of samples including fluorescently tagged particles.

2. Description of the Related Art

The following description and examples are not admitted to be prior art by virtue of their inclusion in this section.

Generally, flow cytometers are devices configured to use optical techniques to measure one or more characteristics of particles or cells in a fluid flowing through the devices. This particle or cell interrogation can be exploited for a number of purposes such as assaying for various chemical and biological molecules. Although flow cytometers offer a number of advantages, the devices have a number of disadvantages. For example, flow cytometers generally utilize optical components that are sensitive to their environment. Furthermore, flow cytometers are typically time consuming to manufacture, complicated to operate, and expensive. These characteristics often restrict the use of flow cytometers to highly trained technicians. Moreover, some samples need to be processed before being run through a flow cytometer and, therefore, significant laboratory resources and other equipment are often needed for the analysis of assays.

It would, therefore, be advantageous to develop systems that measure characteristics of particles or cells in a fluid and are relatively simple to operate. In addition, it would be beneficial for such systems to be capable of performing the measurements without requiring significant laboratory resources for pre-processing of the sample fluids. Furthermore, it would be advantageous for the systems to include components which are substantially insensitive to their environments. Moreover, it would be beneficial for such systems to be relatively inexpensive and not time consuming to manufacture.

SUMMARY OF THE INVENTION

The following description of various embodiments of systems and chip-based flow cytometers are not to be construed in any way as limiting the subject matter of the appended claims.

An embodiment of a system for processing and analyzing biological or environmental samples includes an automated assay preparation module configured to process a sample into a fluid assay with fluorescently tagged particles and a microfluidic analysis module coupled to the automated assay preparation module, wherein the microfluidic analysis module includes a chip-based flow cytometer.

An embodiment of a system for analyzing a fluid sample includes a channel for routing a fluid sample with magnetic particles through the system and a means for inducing a magnetic field along at least a portion of the channel such that the magnetic particles flow within a predetermined region of the fluid sample.

Another embodiment of a system for analyzing a fluid sample includes a channel for routing a fluid sample having fluorescently tagged particles through the system and an illumination subsystem including a light source system and an optical system collectively configured to direct light toward an interrogation region of the channel. The system further includes a measurement subsystem with an aspherical mirror configured to gather fluorescence emitted from the magnetic particles and an examination system for analyzing the collected fluorescence.

An embodiment of a chip-based flow cytometer includes a first input conduit for receiving a fluid sample with fluorescently tagged particles, a second distinct conduit for receiving a sheath fluid, and a fluid flow chamber coupled to the first and second input conduits. The fluid flow chamber is configured to generate a fluid stream with the sample fluid confined within the sheath fluid and having a first dimension of up to approximately 80 microns in a vertical direction perpendicular to the flow of the fluid stream and a second dimension of up to approximately 25 microns in a horizontal direction perpendicular to the flow of the fluid stream.

Another embodiment of a chip-based flow cytometer includes a channel for routing a fluid sample having fluorescently tagged particles through the flow cytometer. In addition, the chip-based flow cytometer includes an illumination subsystem with a light source system and an optical system collectively configured such that individual light sources within the light source system direct light toward different spots within the interrogation region. Moreover, the chip-based flow cytometer includes a measurement subsystem having a collection system configured such that the fluorescent light emitted from the magnetic particles at each of the different spots is collected by a different detector of the collection system and an examination system for analyzing the collected fluorescence.

BRIEF DESCRIPTION OF THE DRAWINGS

Further advantages of the present invention may become apparent to those skilled in the art with the benefit of the following detailed description of the preferred embodiments and upon reference to the accompanying drawings in which.

Figure 1:
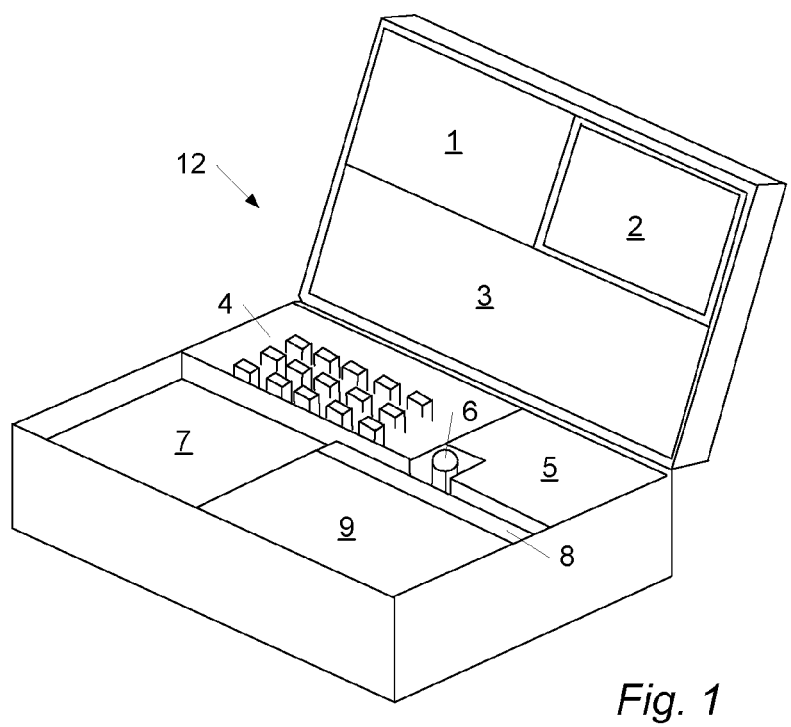
FIG. 1 is a schematic diagram of a portable system configured to process and measure fluidic samples.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, systems for processing and analyzing fluid samples are provided. In general, the systems described herein may be used to process and/or analyze samples including, but not limited to, bodily fluids, environmental samples, and/or biological tissues and substances. Furthermore, as described in more detail below, the systems described herein are configured for processing samples with fluorescently tagged particles infused therein. In some embodiments, the particles may be magnetic. It is noted that the figures are not necessarily drawn to scale. In particular, the scale of some elements in some of the figures may be greatly exaggerated to emphasize characteristics of the elements. In addition, it is further noted that the figures are not drawn to the same scale. Elements shown in more than one figure that may be similarly configured have been indicated using the same reference numerals.

FIG. 1 illustrates an exemplary portable system for processing and analyzing fluidic samples. In general, the portable systems described herein may include a processing module, an analysis module, and support modules including, but not limited to, fluidics, fluid storage, power supply, computer hardware (and software), display, and a human interface. FIG. 1 illustrates portable system 12 opened showing an exemplary assortment and placement of modules within a base portion and lid of the system. It is noted, however, the portable systems described herein are not necessarily so limited. In particular, other portable systems having fewer or more modules than the ones described in reference to FIG. 1 may be considered. In addition or alternatively, one or more of the modules described in reference to portable system 12 may be arranged in a different position relative to the other modules. For instance, in some cases, portable system 12 may include different modules or no modules in the lid of the system. In other cases, portable system 12 may not include a lid. In any case, the "portability" of the systems described herein may refer to systems being able to be transported by a user.

As shown in FIG. 1, portable system 12 may include computer 1, display 2, battery 3, and human interface 9, all of which may include any suitable component known in the art for the corresponding device. In some cases, computer 1 may be used to convert measurements taken by microfluidic analysis module 5 (e.g., fluorescence measurements, light scatter measurements, etc.) into values which reflect the amount of analyte present in a sample. In addition or alternatively, computer 1 may be used to control the operations of other components within portable system 12, such as but not limited to the components within processing module 6 and microfluidic analysis module 5. In any case, display 2 may be used to present measurement values and/or converted values to a user. In addition or alternative to the inclusion of battery 3, portable system 12 may be equipped with an AC/DC converter. Human interface 9 may be configured such as to control the initiation of processing or analyzing a fluid and/or manipulate the measurements acquired during analysis. As further shown in FIG. 1, portable system 12 may include reagent cartridge storage 4, processing module 6, microfluidic analysis module 5, sheath fluid module 7, and pump module 8, each of which may be configured as described further herein. In some embodiments, the systems described herein may include one or more interchangeable modules that can be replaced such that the systems can be used for different applications. Possible applications of the embodiments described herein include, but are not limited to, a medical diagnostic device or environmental biological sampler. The modular nature of the embodiments allows for easy and inexpensive reconfigurations from one application to another.

Figure 2:
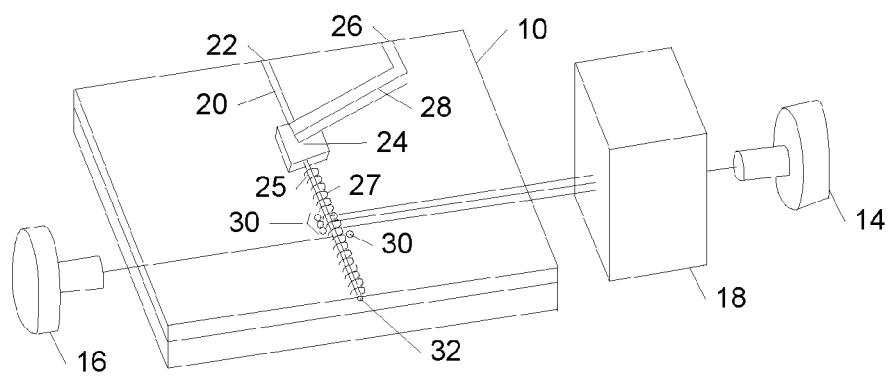
FIG. 2 is an isometric view of an exemplary embodiment of a microfluidic analysis module that may be included in the portable system referenced in FIG. 1.

In some embodiments, microfluidic analysis module 5 may include a highly integrated chip-based flow cytometer. More specifically, microfluidic analysis module 5 may include a fixed configuration of some or all of the following components fabricated as semiconductor devices: microfluidic channels, photo multiplier tubes, avalanche photodiodes, pin photo diodes, magnetic transducers, optical filters, lenses, mirrors, resonators, optical gain mediums, and excitation sources such as light emitting diodes, resonant cavity light emitting diodes, diode lasers, vertical cavity surface emitting lasers, phosphorescent materials, radioactive materials, plasmas, and acoustic sources. An exemplary configuration of components for microfluidic analysis module 5 is illustrated in FIG. 2. In particular, FIG. 2 illustrates an embodiment of microfluidic analysis module 5 in which fluidic channels, fluidic focusing components, and collection optics are fixedly arranged within semiconductor substrate 10. In some embodiments, microfluidic analysis module 5 may also include light sources (e.g., light sources 14 and 16 in FIG. 2) and optical components (e.g., beam splitter 18 in FIG. 2) fixedly arranged relative to each other and semiconductor substrate 10. In alternative cases, light sources 14 and 16 and/or beam splitter 18 may be integrated within semiconductor substrate 10.

In general, the chip-based flow cytometer of microfluidic analysis module 5 may be configured to measure one or more characteristics of fluorescently tagged particles which are infused within a fluid flowing through the flow cytometer. More specifically, the chip-based flow cytometer may be configured to measure fluorescence emitted by particles within a sample and use the measurements to determine the presence of a reagent associated with the particles. Based on the presence or absence of the reagent, the system can determine the presence or absence of one or more analytes in the samples and may also determine other characteristics of the one or more analytes such as concentration within the sample. In some cases, light scattering characteristics of the particles may be additionally measured by the chip-based flow cytometer to determine the presence/absence of analyte within a sample and/or classifications of the particles.

In general, the term "particle" as used herein may refer to any substrate used for the analysis of chemistry, biological, and environmental assays and may specifically refer to articles used to provide and/or support molecular reactions for the qualification and/or quantification of an analyte of interest including but not limited to kinase activity. In addition, the term "particle" may reference articles of a broad range of sizes, such as but not limited to articles having dimensions between approximately 1 nm approximately 300 μm. Hence, the term "particle" may refer to a number of different materials and configurations, including but not limited to particles, beads, polystyrene beads, microparticles, gold nanoparticles, quantum dots, nanodots, nanoparticles, composite particles (e.g., metal-polymeric particles or magnetite-polymeric particles), nanoshells, nanorods, nanotubes, microbeads, latex particles, latex beads, fluorescent beads, fluorescent particles, colored particles, colored beads, tissue, cells, micro-organisms, spores, organic matter, any non-organic matter, or any combination thereof. Accordingly, any of such terms may be interchangeable with the term "particle" used herein.

Recent innovations have allowed simultaneous analysis of multiple assays through the use of distinguishable carrier particles. One example of such an assay system is the xMAP™ technology that is commercially available from Luminex Corporation of Austin, Tex. The xMAP technology uses a family of dyed particles onto which one or more assay-specific reagents may be applied (e.g., by coupling to one or more functional groups on the surface of the particles). The particle platform employs different sets of particles distinguishable by fluorescence. For example, the sets of particles may be distinguishable by wavelength of fluorescence, intensity of fluorescence, ratio of intensities of fluorescence at different wavelengths, etc. In general, the variation of fluorescence may be integrated by different dyes and/or fluorophores incorporated into the particles and/or are coupled to a surface of the particles. In some embodiments, the sets of particles may be additionally distinguishable by size and/or shape. In any case, a particle platform having distinguishable carrier particles is generally advantageous because it uses fluid based kinetics to bind several different analytes to the assay-specific reagents. In particular, the particles can be used to test for more than 100 different analytes in a sample.

In general, each of the different sets of particles may have a different reagent coupled to the particles. The different reagents may selectively react with different analytes in the fluid sample. In other words, each of the different reagents may react with one analyte in a sample, but may not substantially react with any other analytes in the sample. In some cases, one or more additional detectable reagents may be allowed to react with one or more of the analytes. The one or more additional reagents may be detectable (and possibly distinguishable) by fluorescence (e.g., wavelength of fluorescence, intensity of fluorescence, etc.). In addition to the enhanced reaction kinetics, the use of a multiplexed particle platform advantageously allows a user to simply add or remove one or more subsets of particles, to or from the population to which the sample is exposed, to change the tests being performed in a panel.

Figure 3:
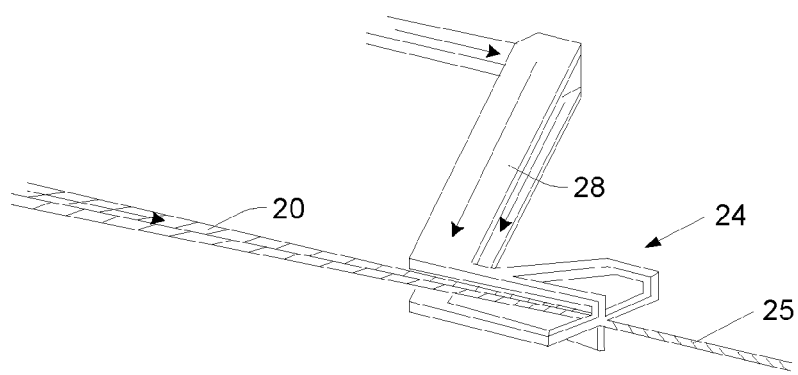
FIG. 3 is an isometric view of an exemplary embodiment of a fluid focusing subsystem that may be included in the microfluidic analysis module referenced in FIG. 2.

Turning back to FIG. 2, the operation of the flow cytometer may include introducing the sample on which an assay is being performed into input conduit 22. Prior to being illuminated, the sample may, in some embodiments, be combined with a sheath fluid in fluid flow chamber 24 as shown in FIG. 2. The sheath fluid may be pumped by pump module 8 from sheath fluid module 7, enter the analysis module through input conduit 26, and may flow through sheath fluid channel 28 to fluid flow chamber 24. Therefore, the sample and sheath fluids are injected into the flow cytometer through separate input ports. The two fluids meet in fluid flow chamber 24 and the chamber is configured such that a fluid stream is generated which includes the sheath fluid encompassing the sample fluid. An exemplary configuration of fluid flow chamber 24 is illustrated in FIG. 3. It is noted, however, that other fluid combining techniques may be used for the systems described herein including, but not limited to, hydrodynamic focusing, electrokinetic focusing, acoustic wave focusing, and magnetic focusing. Consequently, the systems described herein are not necessarily limited to the depictions of FIGS. 2 and 3. For example, a fluid combining device that may be additionally or alternatively used with the flow cytometer of microfluidic analysis module 5 may be a hydrodynamic focusing cuvette arranged at a joined interface of channels 20 and 28. The cuvette may perform highly uniform focusing and confinement of the sample stream in all directions that lie perpendicular to the axis of the cuvette.

As shown in FIG. 3, fluid flow chamber 24 may be configured to confine the sample fluid within the sheath fluid in both the vertical and horizontal directions. In this manner, the sheath fluid may surround the sample fluid from all sides. This physical confinement technique confines the sample fluid to approximately the center of the stream generated from the fluid flow chamber 24 and, in some cases, narrows the sample fluid to a fraction of its previous diameter. By reducing the diameter of the sample fluid, particles in the flow are pulled farther apart along the fluid channel allowing for easier interrogation. It has been found, however, that the incorporation of fixed chip-based components within a flow cytometer offers notable measurement precision even with relatively wide fluid streams. Thus, fluid flow chamber 24 may be configured to narrow a sample fluid diameter to a lesser degree than in conventional systems. For instance, fluid flow chamber 24 may be configured to reduce the diameter of the sample fluid within channel 25 to less than 10 times its diameter within channel 20 or, more specifically, about 5 times its diameter within channel 20. Narrowing the sample fluid to a lesser degree may advantageously reduce the amount of sheath fluid needed, reducing costs and waste.

Another manner to describe the confinement adaptations of fluid flow chamber 24 is to specify exemplary dimensions of the sample stream within the fluid stream it is configured to generate. For example, fluid flow chamber 24 may be configured such that the sample fluid has a first dimension of up to approximately 80 microns in a vertical direction perpendicular to the flow of the fluid stream (i.e., a first dimension of up to approximately 80 microns in the z-direction when flow of the fluid is in the x-direction). In addition, fluid flow chamber 24 may be configured such that the sample fluid has a second dimension of up to approximately 25 microns in a horizontal direction perpendicular to the flow of the fluid stream (i.e., a second dimension of up to approximately 25 microns in the y-direction when flow of the fluid is in the x-direction). Larger or smaller dimensions for the sample fluid, however, may be considered as well, depending on the design specifications of the flow cytometer.

In any case, the fluid stream generated from fluid flow chamber 24 may flow through channel 25 as shown in FIGS. 2 and 3. More specifically, the fluid stream generated from fluid flow chamber 24 may flow to an optical interrogation region of the flow cytometer, denoted as collection optics 30 along channel 25 in FIG. 2. After passing through the optical interrogation region, the combined sample and sheath fluids may exit the analysis module through outlet 32. In some embodiments, fluid channel 25 may be configured to be non-removable. In other words, portable system 12 may include a fluid channel that is not disposable. In contrast, the fluid channels in existing chip scale technologies are designed to be formed in a removable substrate so that the fluid channels may be disposable. Therefore, a distinguishing feature of the embodiments described herein is that the fluid channel may be neither removable nor disposable. In some embodiments, it may be advantageous to arrange the sample fluid of the generated fluid stream in a predetermined location of fluid channel 25. More specifically, it may be advantageous to have the particles within the sample fluid arranged in a relatively predictable location in channel 25 (e.g., approximately the center of the fluid channel) such that the angles at which light may be directed toward the particles and emissions collected from the particles for optimum operation of the flow cytometer may be anticipated.

In order to accommodate the arrangement of particles within a predetermined location of channel 25, the systems described herein may, in some embodiments, include means 27 for inducing a magnetic field along at least a portion of channel 25 as shown in FIG. 2. For example, the flow cytometer of microfluidic analysis module 5 may include a solenoid coil wrapped around fluid channel 25. It is noted that the systems described herein are not necessarily limited to such a magnetic field inducing mechanism. In particular, other means for inducing a magnetic field along at least a portion of channel 25 may be additionally or alternatively used. In any case, means 27 may, in some embodiments, extend along the entirety of fluid channel 25 (i.e., between fluid flow chamber 24 and output 32). In yet other embodiments, means 27 may extend along a limited section of fluid channel 25. For example, means 27 may, in some embodiments, be restricted to a portion of fluid channel 25 extending between fluid flow chamber 24 and through the interrogation region denoted by collection optics 30. In yet other embodiments, means 27 may, in some embodiments, may be restricted to a shorter portion of fluid channel 25 such as in close proximity to and including the interrogation region. In any case, means 27 may be configured to generate a magnetic field around fluid channel 25 in some embodiments. Alternatively, means 27 may be configured to generate a magnetic field along less than the circumferential periphery of fluid channel 25.

As noted above, the sample fluid surrounded by the sheath fluid flows from fluid flow chamber 24 to the optical interrogation region of fluid channel 25. In the optical interrogation region, light sources 14 and 16 illuminate the sample fluid. Fluorescence emitted by the particles within the sample fluid is collected by collection optics 30 and directed to one or more detectors of the flow cytometer, which may be fixedly arranged relative to substrate 10 at an angle anticipated for the emissions. Therefore, the optical interrogation region of fluid channel 25 is defined by the locations along the fluid channel that are illuminated by the light beams and the locations along the fluid channel at which the collection optics collect light (e.g., fluorescent light, scattered light, or some combination thereof). As shown in FIG. 2, the light from light sources 14 and 16 may be directed to different locations along fluid channel 25 that are spaced apart from each other. Such locations may be referred to herein as interrogation spots. The interrogation spots may include any suitable spacing, depending on the design specifications of the flow cytometer.

Figure 4:
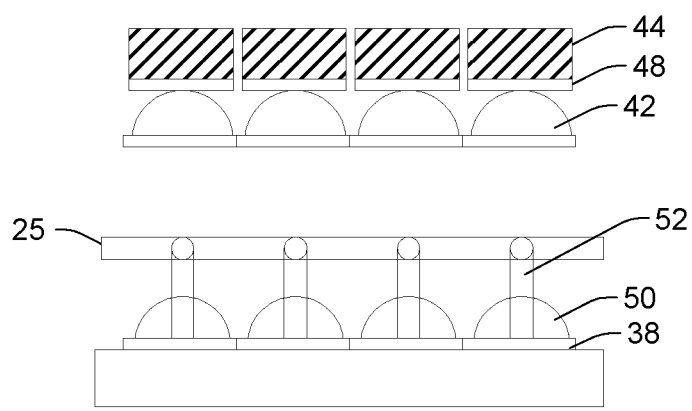
FIG. 4 is a side view of an exemplary collection of light sources, collection optics and detectors included in the microfluidic analysis module referenced in FIG. 2.

To facilitate multiple interrogation spots, the flow cytometer may, in some embodiments, include a beam splitter between one or more of light sources 14 and 16 and fluid channel 25, such as shown with the inclusion of beam splitter 18 in FIG. 2. In general, beam splitter 18 may include any suitable optical element/s that is configured to split light into two or more different beams of light. Thus, beam splitter 18 is not restricted to the depiction of splitting light into three beams as illustrated in FIG. 2. Furthermore, the cytometer shown in FIG. 2 is not restricted to using beam splitter 18 with respect to light source 14. In particular, the flow cytometer may additionally or alternatively include a beam splitter positioned to split light directed from light source 16. In some embodiments, it may be advantageous to include multiple light sources within the flow cytometer, particularly one for each interrogation spot. As such, in some cases, the flow cytometer may not include beam splitters. In particular, due to the miniaturization of device components within the chip-based flow cytometer, the detectors of the flow cytometer may need to collect full emissions from an interrogation spot in order to adequately measure the fluorescence of a particular channel. Consequently, in addition to including a different light source for each interrogation spot, the flow cytometer may include a different detector for each interrogation spot. Furthermore, the flow cytometer may include a different set of optical components, including but not limited to mirrors, lens, and/or filters, for each interrogation spot. An exemplary arrangement of light sources, optical elements, and detectors used for the flow cytometers described herein is shown in FIG. 4 and described in more detail below.

In any case, although FIG. 2 shows the inclusion two light sources with the flow cytometer depicted therein, it is to be understood that the flow cytometer may include any number of light sources within its illumination subsystem. Any suitable light sources may be employed within the flow cytometer, such as but not limited to light emitting diodes (LEDs), lasers, arc lamps, fiber illuminators, light bulbs, incandescent lamps, or any other suitable light sources known in the art. In addition, the one or more light sources may be configured to emit monochromatic light, polychromatic light, broadband light, or some combination thereof. Furthermore, light from the one or more light sources may be directed to fluid channel 25 in any suitable direction (e.g., by suitable positioning of the light sources and/or by using suitable light directing optical elements). As such, although FIG. 2 illustrates light sources 14 and 16 directing light toward fluid channel 25 at substantially opposite directions, the systems described herein are not necessarily so limited.

As noted above, FIG. 4 illustrates an exemplary arrangement of light sources, optical elements, and detectors used for the flow cytometers described herein. The exemplary arrangement includes four light sources 38, which are substantially perpendicularly aligned with four distinct collection optics 42 and four distinct detectors 44. In other words, collection optics 42 are arranged to collect light emitted from the particles within the sample fluid along a direction that is substantially perpendicular to a direction at which light from light sources 38 is directed. Collection optics 42 may include one or more refractive optical elements, each of which is configured to collect light fluoresced and/or scattered from a corresponding location along the fluid channel. Detectors 44 may include any suitable detectors such as but not limited to silicon avalanche photodiodes. In some cases, each of light sources 38 may be configured to emit light having substantially the same wavelength. In other embodiments, however, one or more of light sources 38 may be configured to emit light at a different wavelength than the light emitted by other of light sources 38.

In some embodiments, the systems described herein may include filters 48 positioned in between collection optics 42 and detectors 44. Filters 48 may include any suitable optical elements known in the art such as but not limited to spectral filters that are configured to limit the wavelength(s) of the light detected by detectors 44. As further shown in FIG. 4 the exemplary arrangement may include illumination optics 50. Illumination optics 50 may include a number of refractive optical elements, which may include any suitable refractive optical elements known in the art. Each of the refractive optical elements of illumination optics 50 may be configured to collimate one of light beams 52 generated by light sources 38 of semiconductor light emitters. In this manner, the light beams may be directed to channel 25 along directions that are substantially parallel to each other. Although FIG. 4 is shown to include four sets of components, it is to be understood that the systems described herein may include any suitable number of component sets.

Figure 5:
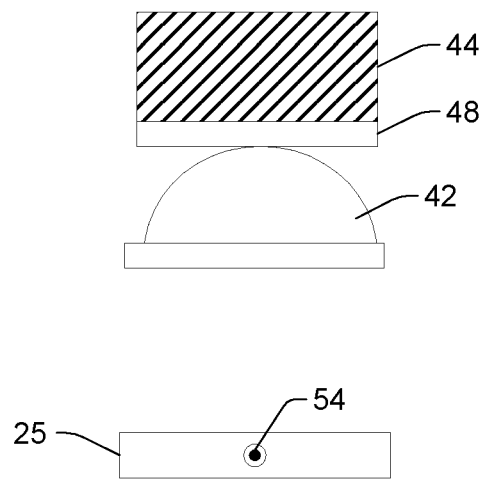
FIG. 5 illustrates a cross-sectional view of an exemplary system configured for preparing a fluid assay.

FIG. 5 illustrates a different exemplary arrangement of light sources, optical elements, and detectors used for the flow cytometers described herein which employs a configuration referred to herein as 90 degree off-axis illumination. In such configurations, the system may include an optical element configured to direct light to fluid channel 25 at an angle that is about 90 degrees from the angle at which light sources 38 are configured to direct light to the fluid channel. Alternatively, light sources 38 may be arranged to direct light at a 90 degree angle to fluid channel 25. More specifically, a mirror or other suitable optical element may be arranged such that light directed from light sources 38 strikes fluid channel 25 at a direction that is substantially perpendicular to both the fluid channel and the optical stack that includes collection optics 42 and detectors 44 such that the 90° side scatter component of the light is collected and detected for the optical interrogation method. To illustrate such a configuration, FIG. 5 depicts the exemplary arrangement of components along an x-z plane, wherein fluid flow in channel 25 is in the x-direction and the position of the optical elements and detectors are in the z-direction relative to channel 25. In such embodiments, the light source/s is arranged in the y-direction relative to channel 25 and, therefore, is not depicted in FIG. 5. Rather, light beam 54 directed from the light source/s is shown coming out of the page denoting the 90 degree off-axis illumination. Although FIG. 5 illustrates a single set of components, it is to be understood that the systems described herein may include any suitable number of distinct sets of components as similarly described for the configuration depicted in FIG. 4.

In some embodiments, the flow cytometers described herein may include an aspherical mirror for gathering the fluoresced and/or scattered light. In particular, an aspherical mirror may advantageously distort the collected light to a level within a range of light which the detectors may be capable of detecting. More specifically, the detection range of the detectors cannot generally be scaled down in the same manner as the other devices in the chip-based flow cytometer and, thus, it may be beneficial to incorporate an aspherical mirror to alter collected light into a range which is within the ability of the detectors. In some embodiments, the aspherical mirror may be coated with an anti-reflective coating (ARC) to aid in rejection of unwanted wavelengths, increasing the signal-to-noise ratio of the collected light. In some embodiments, an ARC that is configured to reflect fluorescent emissions rather than scattered light may be employed. In other embodiments, an ARC that is configured to reflect scattered light in addition to fluorescent emissions may be employed. Such configurations may be facilitated by the wavelength range the ARC is configured to reflect. As shown in FIG. 5, aspherical mirror 56 may be arranged on the side of fluid channel 25 opposing collection optics 42, filter 48, and detector 44. In this manner, aspherical mirror 56 may increase the amount of light collected by the flow cytometer. It is noted that the configuration of components described in reference to FIG. 4 may also include an aspherical mirror.

In response to the excitation, particles in the sample flow may fluoresce thereby signaling the presence of at least one of the following materials with the sample fluid including, but not limited to, particle identification dye, enzymes, proteins, amino acids, DNA, RNA, antibodies, and antigens. In addition to direct fluorescence being used as an indicator, the presence of a magnetic field may be used to further modulate the excitation of the particle or emission from the particle. One advantageous feature of the analysis module is the ability to measure or "read" and classify fluorescent particles in real time using output generated by multiple channels of the analysis module.

In some embodiments, the system may be configured to perform the measurements by gating a response of particles to illumination as the sample flows through the interrogation region in fluid channel 25. For example, as the sample flows through the optical interrogation region of the analysis module, gating the response of the particles to illumination may be performed by collecting and detecting the fluorescence and/or scattered light with the collection optics and the one or more detectors and comparing the output of the one or more detectors to a predetermined threshold. If the output is above the predetermined threshold, the system may determine that a microsphere caused the fluorescence and/or scattered light and therefore that the microsphere is passing through the interrogation region. As such, the fluorescence and/or scattered light corresponding to the microsphere may be recorded or otherwise processed by the system (e.g., processed for real-time classification).

In another embodiment, the system may be configured to perform the measurements by distinguishing between single particles flowing through the interrogation region of fluid channel 25 and multiple particles flowing through the interrogation region at substantially the same time. For example, scattered light detected by one or more detectors of the analysis module may generally be proportional to the volume of the particles that are illuminated by the one or more light sources. Therefore, output of the one or more detectors may be used to determine a diameter and/or volume of the particles that are in the optical interrogation region. In addition, the output of the one or more detectors and the known size or volume of the particles may be used to identify more than one microsphere that are stuck together or that are passing through the optical interrogation region at approximately the same time. Therefore, such particles may be distinguished from other sample particles and calibration particles. Furthermore, the output of the one or more detectors may be used to distinguish between sample particles and calibration particles if the sample particles and calibration particles have different sizes.

As noted above, portable system 12 may, in some embodiments, include processing module 6. Such a module may generally be configured to process samples before the samples are introduced into microfluidic analysis module 5. The processing may include any one or more of particle size filtering, centrifuging, analyte isolation, analyte amplification, washing of the sample, cell lysing, clotting factor neutralization, pH regulation, temperature cycling, reagent mixing, and assay reaction. Other processing steps may be considered as well. Exemplary configurations of systems which may be used for processing module 6 are illustrated in FIGS. 6-9 and described in more detail below. Exemplary components which may be used to support such systems are illustrated in FIGS. 10-11c and 16-18. In addition, methods for operating such process modules are outlined in flowcharts of FIGS. 12-15. In yet other embodiments, portable system 12 may not include processing module 6. In such cases, portable system 12 may be configured to analyze raw samples (i.e., samples which have not be pre-processed) or samples which have been pre-processed independent of portable system 12.

Figure 6:
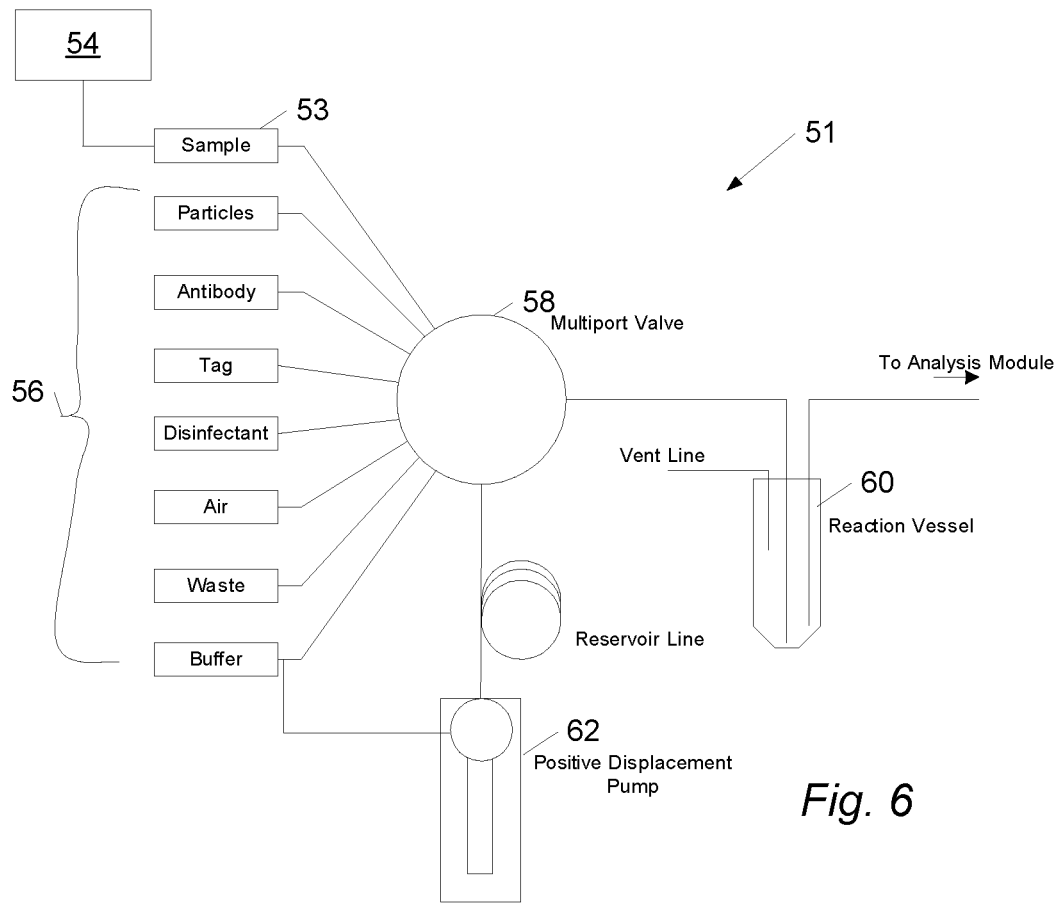
FIG. 6 illustrates a schematic drawing of a different exemplary system configured for preparing a fluid assay.
Figure 7:
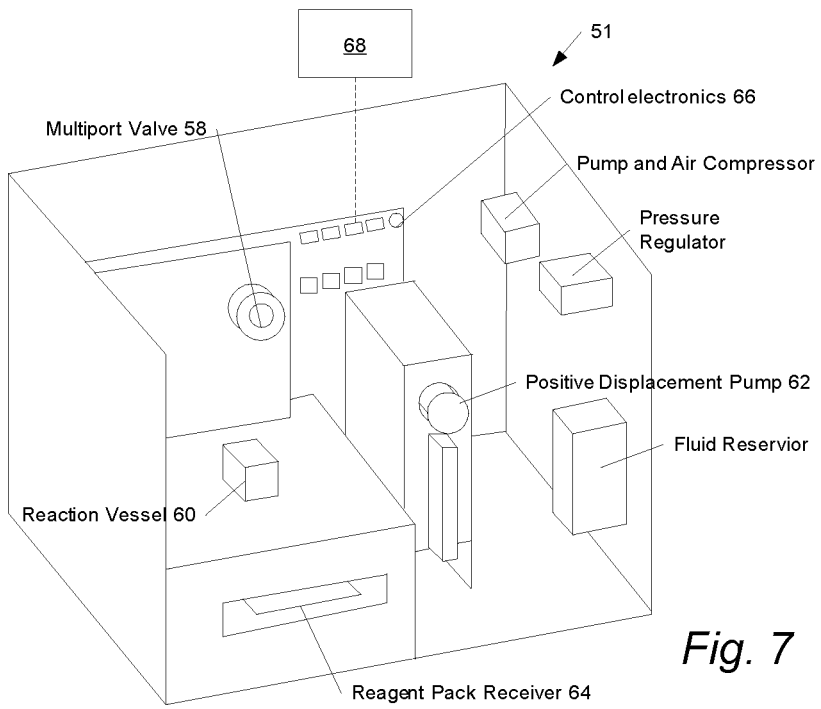
FIG. 7 illustrates a prospective view of an exemplary system which follows the schematic layout of FIG. 6.

FIG. 6 illustrates a schematic drawing of fluid assay preparation system 51 and FIG. 7 illustrates a perspective view of an exemplary configuration for fluid assay preparation system 51. As shown in FIGS. 6 and 7, fluid assay preparation system 51 may include sample inlet 53 for introducing a fluid sample into system 51. In some embodiments, fluid assay preparation system 51 may include sample preprocessing system 54 for processing the sample prior to being introduced into inlet 53. The preprocessing system may be configured to perform any of the steps described below in reference to FIG. 13 or any state transformation steps. For example, a wetted wall cyclone may be considered for condensing a gas sample into a liquid. Fluid assay preparation system 51 further includes reagent pack 56 including a plurality of vessels each filled with different reagents. Reagent pack 56 may also include one or more vessels for receiving waste streams from the fluid assay preparation performed by system 51. It is noted that the reagents noted in FIG. 6 are exemplary and fluid assay preparation system 51 is not necessarily so limited. For processing a sample, reagent pack 56 may be arranged within reagent pack receiver 64 (shown in FIG. 7) and coupled to multi-port valve 58, which in turn may be coupled to reaction vessel 60 by fluidic lines. In addition, input 53 may be coupled to multi-port valve 58. In an alternative embodiment, fluid assay preparation system 51 may include one or more individual valves respectively coupled to the vessels of reagent pack 56 and/or input 53. In any case, reagent pack 56 may be stored within reagent storage module 4 of portable system 12 prior to being used by processing module 6.

As shown in FIGS. 6 and 7, fluid assay preparation system 51 may further include control electronics 66 and pump 62 coupled to multi-port valve 58. Alternatively, fluid assay preparation system 51 may use pump module 8 of portable system 12. In either case, control electronics 66, pump 62 or pump module 8, and multi-port valve 58 may be collectively configured such that the sample introduced within input 53 and the reagents within reagent pack 56 may be introduced into reaction vessel as well as drawn therefrom, preferably at separate stages within the fluid assay preparation process. A more detailed description of exemplary routings of the reagents to and from reaction vessel 60 is provided in reference to FIGS. 12-15 below.

As shown in FIG. 7, fluid assay preparation system 51 may further include storage medium 68 coupled to control electronics 66. In general, storage medium 68 may include program instructions which are executable by a processor for automating the preparation of a fluid assay, such as but not limited to the steps described in below in reference to the flowcharts depicted in FIGS. 12-15. The storage medium may include but is not limited to a read-only memory, a random access memory, a magnetic or optical disk, or a magnetic tape. The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired. In some embodiments, storage medium 246 may include a processor for executing the program instructions. In other embodiments, however, storage medium 246 may be configured to be coupled to a processor (e.g., by a transmission medium). In either case, the processor may take various forms, including a personal computer system, mainframe computer system, workstation, network appliance, Internet appliance, personal digital assistant (PDA), a digital signal processor (DSP), field programmable gate array (FPGA), or other device. In general, the term "computer system" may be broadly defined to encompass any device having one or more processors, which executes instructions from a memory medium. It is noted that storage medium 68 is shown coupled to control electronics 66 by dotted lines in FIG. 7 to indicate that the connection may be either fixed or detachable.

In some embodiments, fluid assay preparation system 51 may be configured for multiple use operation and, therefore, may be reusable. In particular, fluid assay preparation system 51 may be configured to prepare multiple fluid assays, including those of the same or different makeup. In other embodiments, fluid assay preparation system 51 may be configured for single use operations and, therefore, may be configured to be disposable. In either case, reagent pack 56 may be configured for single or multiple use operations. As such, reagent pack 56 may be configured to be disposable (i.e., thrown away after a single fluid assay has been prepared) or may be reusable (i.e., includes reagent amounts sufficient to prepare multiple assays). In the latter case, the vessels of reagent pack 56 may be configured to be disposed after one or more of the reagents are consumed or may be configured to be refilled. In either embodiment, reagent pack 56 allows for easy replacement and may be generally inexpensive to maintain and produce.

Figure 8:
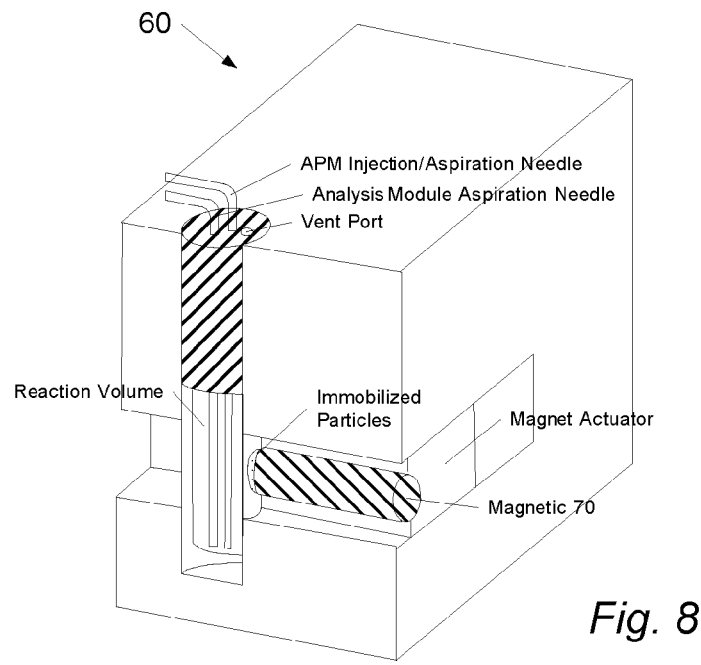
FIG. 8 illustrates a magnified prospective view of the reaction vessel included in the system depicted in FIG. 7.
Figure 9:
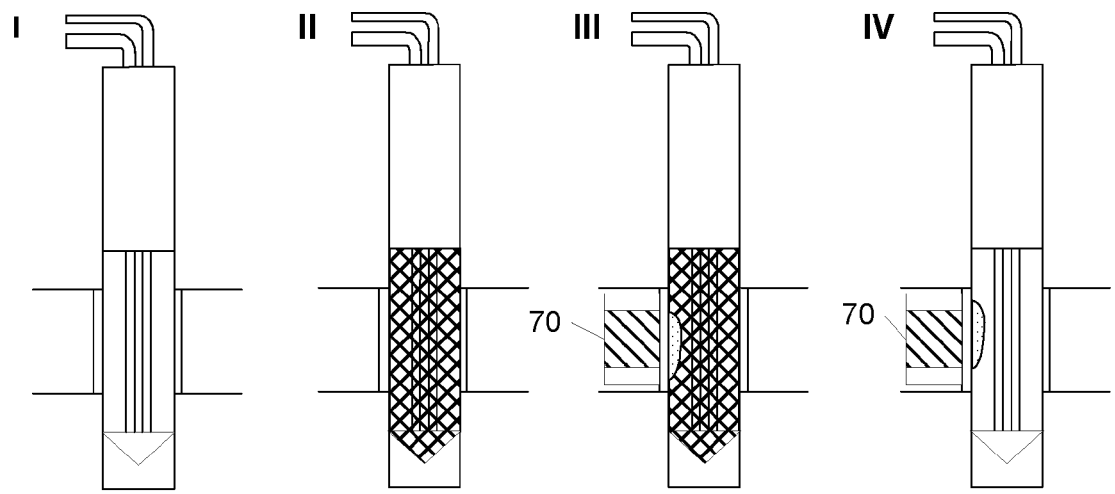
FIG. 9 illustrates cross-sectional view of the reaction volume of the reaction vessel depicted in FIG. 8 during a series of process steps for preparing a fluid assay.

An exemplary configuration for reaction vessel 60 is shown in FIG. 8. As shown in FIG. 8, reaction vessel 60 may include an injection/aspiration needle which may be used to receive and dispatch solutions to and from reaction vessel 60, such as from/to reagent pack 56 and input 53 of fluid assay preparation module 50. Reaction vessel 60 further includes an analysis module aspiration needle, which may be used to dispatch solutions to microfludic analysis module 5. Reaction vessel 60 may further include a vent port, magnet actuator, and magnet 70 as shown in FIG. 8. In some embodiments reaction vessel 60 may further include a sonication system or, more generally, fluid assay preparation system 51 may include a sonication system in proximity to reaction vessel 60. An exemplary manner in which to utilize the magnet actuator and magnet for preparing fluid assay is shown in FIG. 9. In particular, FIG. 9 includes snapshot I in which the reaction vessel volume is empty and, therefore, no fluid sample or reagent has been introduced therein. FIG. 9 further illustrates snapshot II in which the reaction vessel volume is filled with a fluid sample, magnetic particles and, in some cases, one or more reagents. Snapshot III of FIG. 9 illustrates magnet 70 actuated in proximity to the reaction vessel volume to immobilize the magnetic particles and snapshot IV of FIG. 9 illustrates the reaction vessel volume having the fluid removed when the magnetic particles are immobilized. A more detailed description of possible stagings of such an operation during a fluid assay preparation procedure is provided below in reference to FIGS. 12-15.

Figure 10:
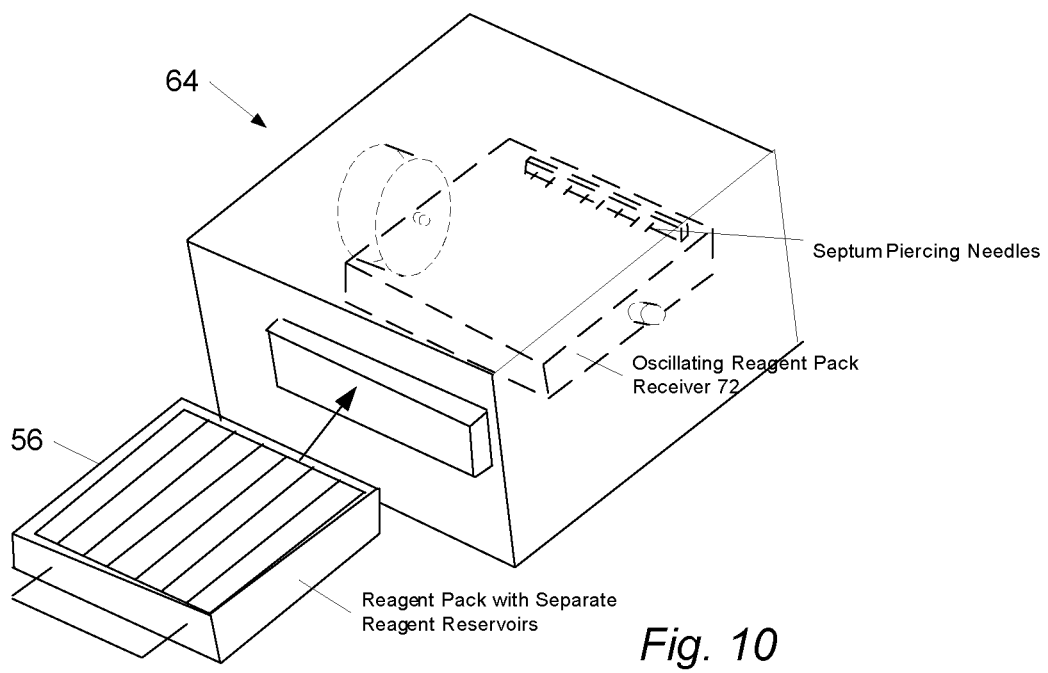
FIG. 10 illustrates a magnified prospective view of the reagent pack receiver of the system depicted in FIG. 7 as well as a reagent pack.
Figure 11A:
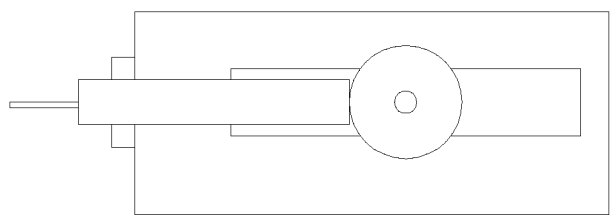
FIG. 11 illustrates cross-sectional view of the reagent pack receiver depicted in FIG. 10 with a reagent pack arranged therein and in a variety of positions to portray oscillation of the reagent pack.
Figure 11B:
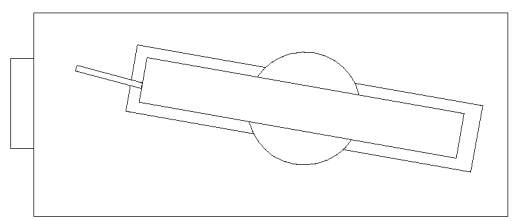
Figure 11C:
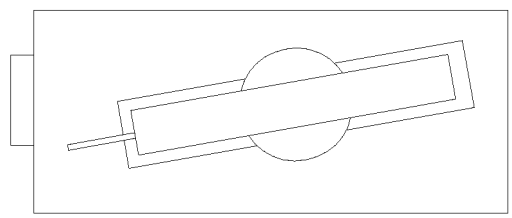

FIG. 10 illustrates an exemplary configuration for reagent pack receiver 64. In particular, FIG. 10 illustrates reagent pack receiver 64 including a slot to receive reagent pack 56. As shown in FIG. 10, the slot may include septum piercing needles to puncture vessels of reagent pack 56 and allow the reagents to be routed to a multi-port valve 58 and/or any valve respectively coupled thereto. The slot and piercing needles allow for easy removal and installation while not requiring the operator to make the fluidic connections. In some embodiments, it may be advantageous to configure reagent pack receiver 64 to tilt back and forth. In particular, it may be advantageous, in some embodiments, to agitate one or more reagents within reagent pack 56. For example, it may be advantageous to agitate particles in solution to reduce clumping in a reagent pack vessel. Such agitation may be incorporated within reagent pack receiver 64 by tilting mechanism 72, various positions of which are illustrated in cross-sectional views of reagent pack receiver 64 in FIGS. 11a-11c. In some embodiments, reagent pack 56 may include a small air bubble within one or more of the reagent vessels to main suspension of components within the respective reagents during oscillation of tilting mechanism 72. The presence of an air bubble may be particularly advantageous for reagents comprising particles to maintain their suspension within the accompanying slurry. In general, the operation of titling mechanism 72 may be continuous, periodic, or sporadic.

Turning to FIGS. 12-15, flowcharts of exemplary methods for preparing fluid assays are shown. As noted above, the storage mediums of the systems described herein may include program instructions which are executable by a processor for automating the preparation of a fluid assay, such as but not limited to the steps described in below in reference to the flowcharts depicted in FIGS. 12-15. Therefore, the methods described in reference to FIGS. 12-15 may be referred to as "computer-implemented methods". It is noted that the terms "method" and "computer-implements method" may be used interchangeably herein. It is also noted that the computer-implemented methods and program instructions of the systems described herein may, in some cases, be configured to perform processes other than those associated with fluid assay preparation and, therefore, the computer-implemented methods and program instructions of systems described herein are not necessarily limited to the depiction of FIGS. 12-15.

Figure 12:
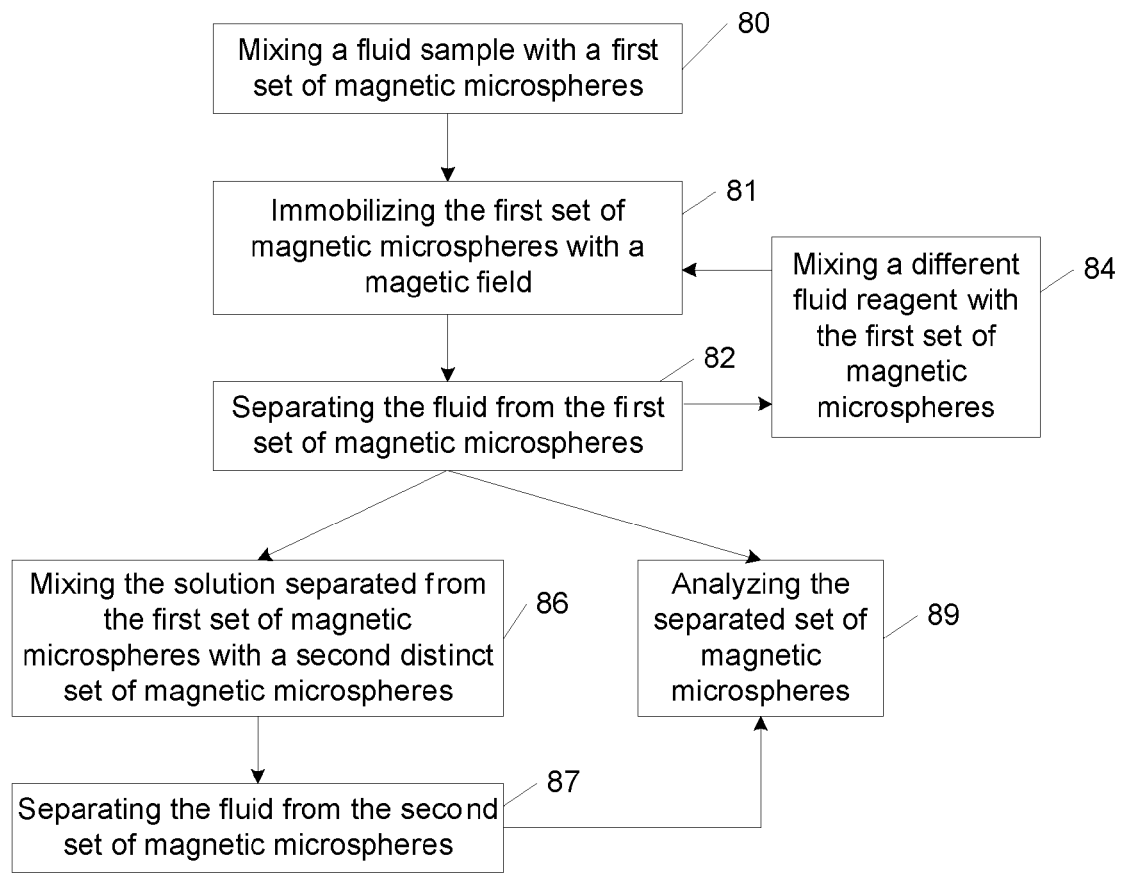
FIG. 12 illustrates a flowchart of an exemplary method for preparing a fluid assay.

As shown in FIG. 12, a method for preparing a fluid assay may include block 80 in which a fluid sample is mixed with a first set of magnetic particles. In reference to system 51 of FIG. 12, the process of block 80 may include infusing a fluid sample into input 53 and routing the fluid through multi-port valve 58 to reaction vessel 60. Subsequent or concurrent thereto, a first set of magnetic particles from reagent pack 56 may be routed to through multi-port valve 58 to reaction vessel 60 to mix with the fluid sample. The fluid sample may, in some embodiments, be preprocessed (i.e. processed prior to being introduced into the systems) such as by the processing steps described below in reference to FIG. 13. In addition or alternatively, the state of the sample may be transformed prior to being introduced into the systems. For example, a solid sample, such as biological tissue, may be suspended within a buffer or an air sample may be condensed into a liquid. In other embodiments, the fluid sample may not be processed prior to being introduced into the systems. In such cases, system 51 may, in some embodiments, be configured to conduct some of the steps described below in reference to FIG. 13. For example, input 53 may, in some cases, include a filter. In addition or alternatively, reagent pack 56 may include a lysing agent for lysing cells within the fluid sample. In such cases, it may be particularly advantageous for system 51 to include a sonication system to insure the cells are lysed after a certain incubation time.

It is noted that other reagents which are known for processing a fluid sample may be additionally or alternatively included within reagent pack 56 for mixing with the magnetic particles and the fluid sample during block 80, such as but not limited to those specific to processing tissue or fluid samples. Consequently, the methods and the systems described herein are not necessarily restricted to the aforementioned processes. In any case, incorporating the aforementioned process steps into system 51 can expand the functionality of process module 6 to perform two processes: the automation of sample processing and the automation of assay preparation. Sample processing is the conversion of a raw sample into a form that is compatible with the desired assay. Assay preparation takes the converted sample and forms a particle based assay.

In general, the first set of magnetic particles referenced for mixing with the fluid sample in block 80 may be configured to react with the fluid sample to capture a desired agent upon the magnetic particles. For example, in some cases, the first set of magnetic particles may be configured to capture nucleic acid from a fluid sample. Such a process is illustrated in the nucleic acid assay flowchart depicted in FIG. 14 and is described in more detail below. Alternatively, the first set of magnetic particles may be configured to capture antigens located in a biological sample (such as tissue or bodily fluid). Such a process is illustrated in the immunoassay flowchart depicted in FIG. 15 and is described in more detail below. It is noted that magnetic particles are referenced herein as reagents and, therefore, may constitute a reagent for which reagent pack 56 may be configured to store for the preparation of a fluid assay. More specifically, the term "reagent" as used herein may generally be referred to herein as a substance used to prepare a product because of its chemical or biological activity.

Subsequent to a predetermined incubation time (which may be assay-specific) for the process described in block 80, the method may continue to block 81 in which the first set of magnetic particles are immobilized with a magnetic field. Such a process may include moving an actuator to which one or more magnets of system 51 is coupled in proximity to reaction vessel 60. Subsequent thereto, the method may continue to block 82 in which the fluid is separated from the first set of magnetic particles. In particular, system 51 may be operated to remove unreacted fluid sample from reaction vessel 60. In some embodiments, the method may continue mixing different fluid reagents with the first set of magnetic particles subsequent to the separation of the magnetic particles from the fluid sample as shown in block 84. In such cases, after mixing with the magnetic particles, the method may reiterate the steps of immobilizing the magnetic particles to separate the different fluid reagents therefrom. For example, in some cases, a washing solution may be mixed with the first set of magnetic particles to remove any unreacted components of the fluid sample previously mixed with the magnetic particles. In addition or alternatively, other reagents may be mixed with the first set of magnetic particles to remove components desirable for analysis, such as for example nucleic acid for nucleic acid assays. In other embodiments, reagents may be mixed with the first set of magnetic particles to add components to the magnetic particles for subsequent analysis, such as immunoassays, for example.

In either case, the first set of magnetic particles may, in some embodiments, be analyzed as shown by the path between blocks 82 and 89. In such cases, the process of block 89 may include moving the first set of magnetic particles to microfluidic analysis module 5. In other embodiments, the method may alternatively mix the solution separated from the first set of magnetic particles (discussed in reference to block 82) with a second distinct set of magnetic particles as shown in block 86 of the flowchart depicted in FIG. 12. For example, in some embodiments, nucleic acid separated from the first set of magnetic particles in a nucleic assay (as described in reference to block 82) may be mixed with a PCR reagent to start a PCR process, which is described in more detail below in reference to FIG. 14. In such a case, the method may continue to block 87 in which the fluid is separated from the second set of magnetic particles, which may include the immobilization of the second set of magnetic particles and the removal of the residual fluid. In some cases, the immobilization of the second set of magnetic particles may be by the same magnet used to immobilize the first set of magnetic particles. In other embodiments, however, the second set of magnetic particles may be immobilized by a different magnet within system 51. Subsequent thereto, the second set of magnetic particles may be analyzed as shown by the path between blocks 52 and 89. Procedures for analyzing the second set of magnetic particles may be generally within the scope described for analyzing the first set of magnetic particles.

Figure 13:
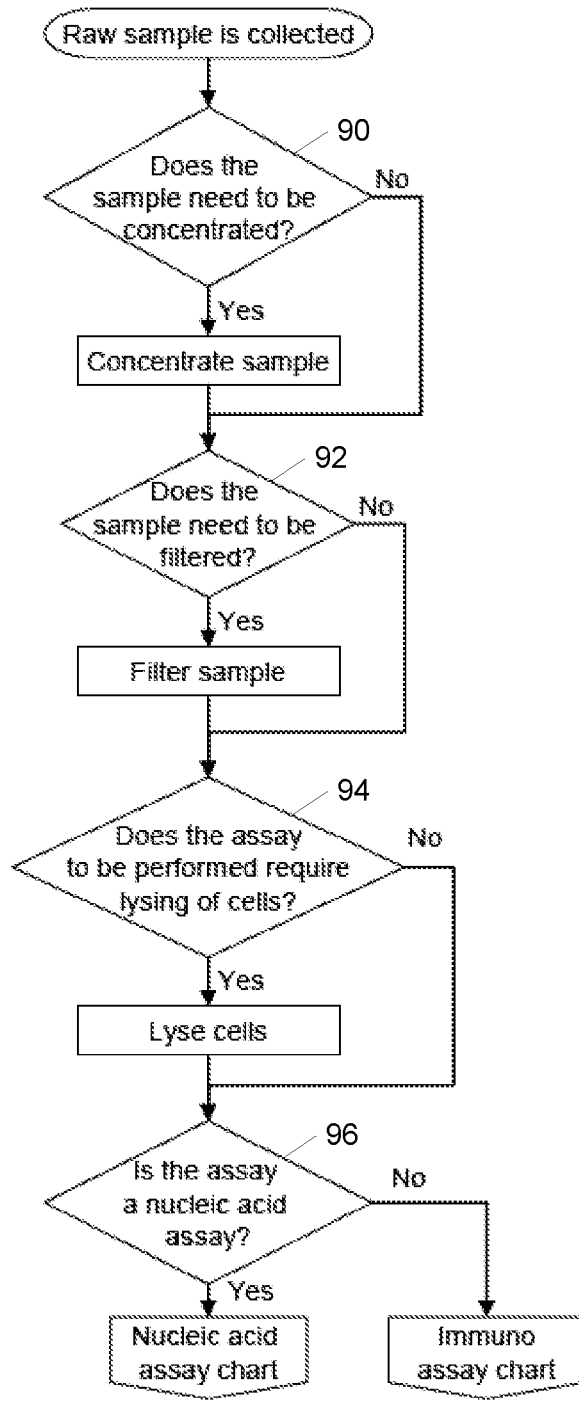
FIG. 13 illustrates a flowchart of an exemplary method for processing a fluid sample into a form that is compatible with a predetermined assay.
Figure 14:
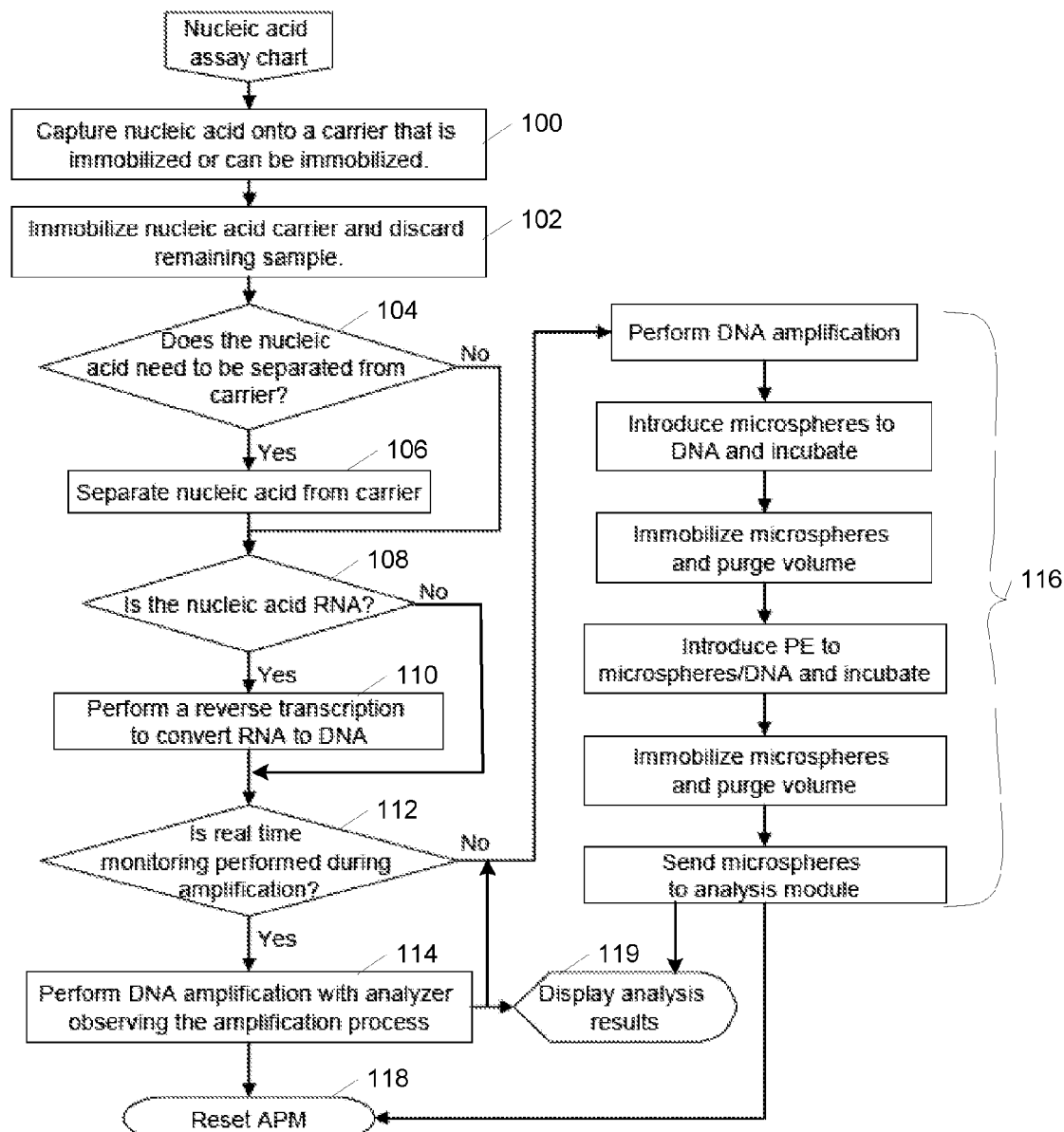
FIG. 14 illustrates a flowchart of an exemplary method for preparing a nucleic acid assay.
Figure 15:
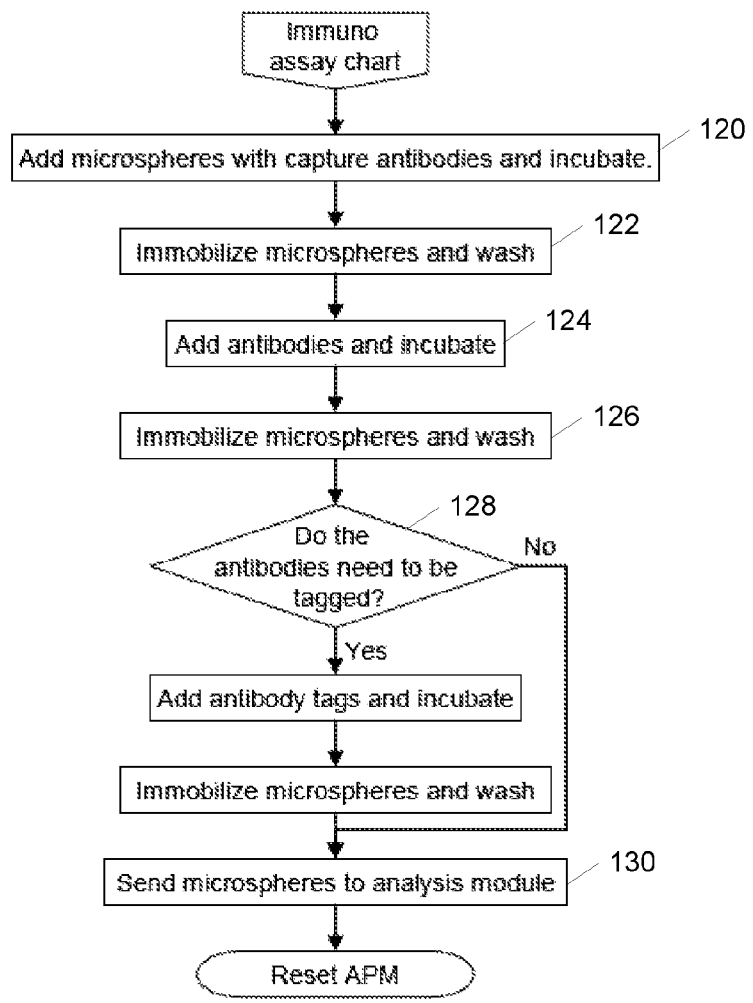
FIG. 15 illustrates a flowchart of an exemplary method for preparing an immunoassay.

As noted above, FIG. 13 illustrates a flowchart of exemplary steps that may be used to process a fluid sample, either prior to or subsequent to being introduced into system 51. In particular, FIG. 13 outlines some determination which may be considered as to how a fluid sample is processed. For example, the flow chart includes block 90 in which a determination of whether the collected sample needs to be concentrated. Examples of embodiments in which a sample may need to be concentrated is when the sample volume needs to be reduced and/or the concentration of analyte within the sample is expected to be too low. FIG. 13 further includes block 92 in which a determination of whether the collected sample needs to be filtered. A filtering process may be advantageous for removing particles which are not of interest or may interfere with the analysis of the sample. In addition to such processes, FIG. 13 includes block 94 in which a determination of whether the assay to be prepared needs the cells of the collected sample to be lysed such that material within a cell can be accessed for analysis. As described above in reference to FIG. 12, the lysing process may be performed prior or subsequent to mixing a fluid sample with a set of magnetic particles. Following the determinations of blocks 90, 92, and 94, the flow chart includes block 96 in which a determination of what type of assay is to be performed. The flowchart depicted in FIG. 13 outlines that a nucleic acid assay or an immunoassay (protein based) may be prepared. Flowcharts outlining exemplary methods for both types of assays are depicted in FIGS. 14 and 15, respectively, and are described in more detail below. It is noted that the methods described in reference to FIGS. 14 and 15 may be performed by any of the system configurations described herein.

As shown in block 100 in FIG. 14, preparation of a nucleic assay may include capturing nucleic acid on to a carrier, such as a magnetic particle, which is or can be immobilized. Thereafter, the nucleic acid carrier may be immobilized and the remaining sample discarded as shown in block 102. In some cases, the nucleic acid carriers may be washed after discarding the sample. Although such a process is not depicted in FIG. 14, it is not necessarily omitted therefrom. In blocks 104 and 106, a determination of whether the nucleic acid needs to be separated from the carrier is made and, if applicable, the nucleic acid is separated therefrom. In such cases, the solution may also be heated to remove the nucleic acid from the particles and, consequently, system 51 may, in some embodiments, include auxiliary heaters. The processes for blocks 100, 102, 104, and 106 may generally be performed by system 51 as described above in reference to processing in reaction vessel 60. After blocks 104 and 106, the method continues to blocks 108 and 110 in which a determination of whether a reverse transaction to convert RNA to DNA needs to be conducted and, if applicable, is performed in block 110.

Thereafter, a determination of whether real time monitoring (analysis) is to be performed with DNA amplification as outlined in block 112. If the determination is to go forward with real time monitoring, a PCR process is performed with a PCR solution which may be provided by Luminex Corporation of Austin, Tex. The PCR process is outlined in block 114 and is formed concurrently with plurality of steps 116 for amplifying DNA, introducing reporter tags (e.g., PE) onto the particles, and analyzing the particles. If a determination is made to forego real time monitoring, the PCR process is not performed, but plurality of steps 116 are performed and when the particles are ready for analysis, they are analyzed by microfluidic analysis module 5. In either case, analysis results may be displayed on display 2 as shown in block 119. In general, the aforementioned RNA to DNA reverse transaction process, the PCR process, and plurality of steps 116 may be performed by system 51 as described above in reference to processing in reaction vessel 60. In the case that system 51 is configured for multiple use operations, the method may continue to block 118 to reset the fluid assay preparation system/module (APM) for a new sample.

FIG. 15 illustrates a flowchart of an exemplary process for preparing an immunoassay. As shown in FIG. 15, the method may include block 120 in which a fluid sample is mixed with magnetic particles having antibodies attached thereto. After an assay-specific incubation period, the magnetic particles are immobilized and washed as noted in block 122 and subsequently additional antibodies are added to the magnetic particles as noted in block 124. Subsequent thereto, the method continues to block 126 in which the magnetic particles are immobilized and washed again. A determination as to whether the antibodies need to be tagged is shown in block 128 followed by the appropriate steps if applicable. Thereafter, the particles are sent to microfluidic analysis module 5 as shown in block 130. In general, each of the process steps leading up to block 130 (i.e., blocks 120, 122, 124, 126, and 128) may be performed by system 51 as described above in reference to processing in reaction vessel 60. In the case that system 51 is configured for multiple use operations, the method may include resetting the fluid assay preparation system/module (APM) for a new sample after block 130.

Figure 16:
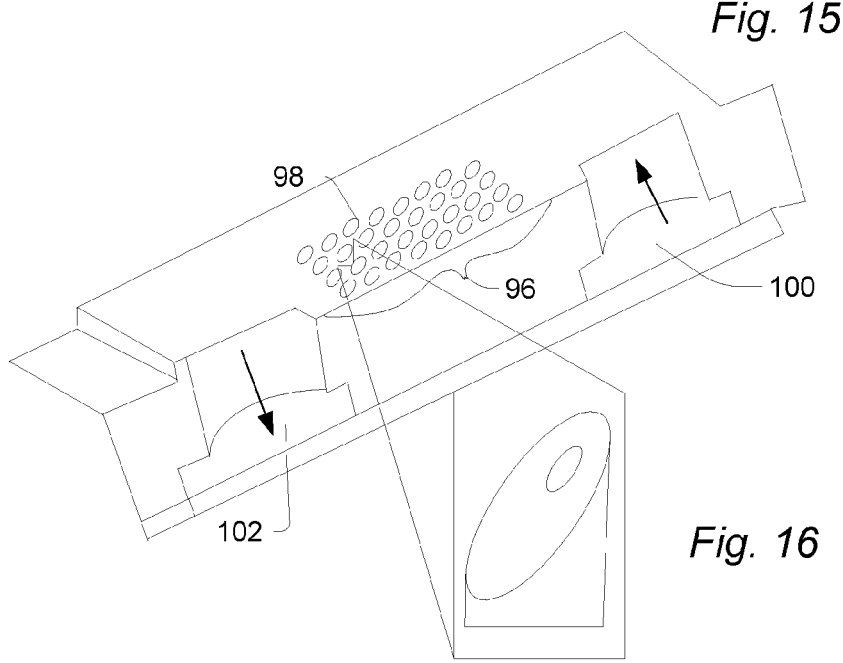
FIG. 16 is an isometric top view of an exemplary embodiment of a reaction cartridge that may be included in the system embodiments described herein.
Figure 17:
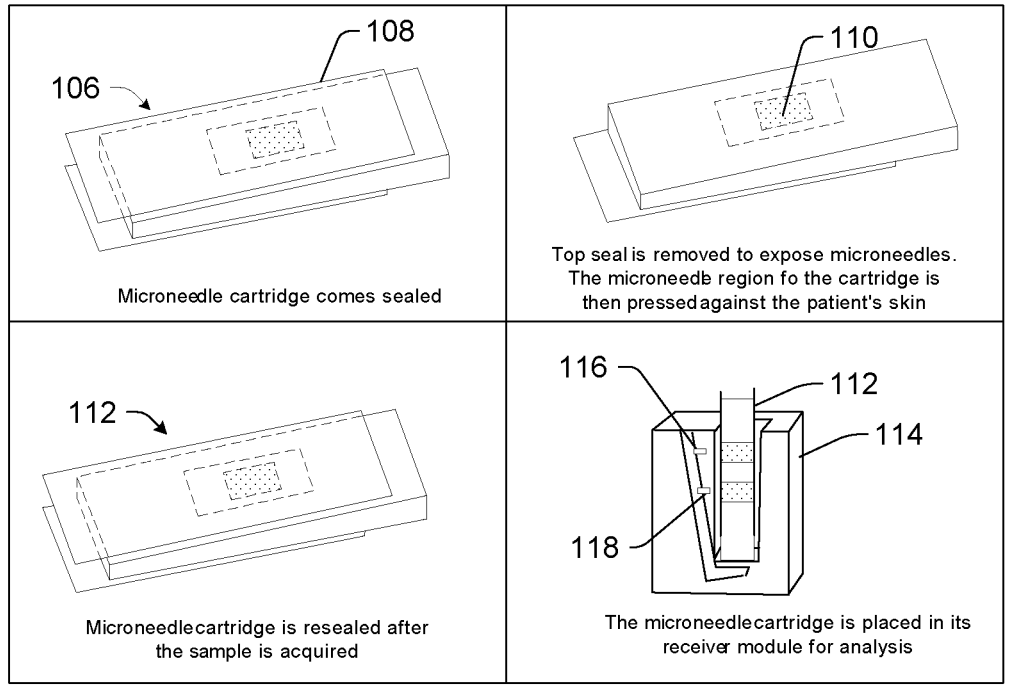
FIG. 17 illustrates different isometric views of another exemplary embodiment of a reaction cartridge, at various times during operation of the reaction cartridge, that may be included in the system embodiments described herein.

In addition to being used with processing module 6, the reagent cartridges described in reference to FIGS. 6-10 can also be used for acquiring a sample. For example, FIG. 16 illustrates a variant of the reaction cartridge that allows for direct sampling with the cartridge. The cartridge shown in FIG. 16 is configured to acquire a sample across blood collection volume 96 by pressing microneedle array 98 against a patient's skin. Sheath fluid may be introduced to the reaction vessel through sheath inlet 100, and the sample may be removed from the reaction vessel through sample outlet 102. Sheath inlet 100 and sample outlet 102 may have any suitable configuration known in the art. The reaction cartridge may also include a removable seal, which may be configured as described herein. The sample flows from the microneedle array into a holding chamber for extraction by the reagent cartridge receiver, one embodiment of which is shown in FIG. 17. In particular, FIG. 17 shows the operation of a reaction cartridge with microneedles. In particular, the microneedle cartridge may be initially sealed as shown by microcartridge 106. Top seal 108 of the microcartridge is removed to expose microneedles 110. The microneedle region of the cartridge is then pressed against the patient's skin. The microneedle cartridge is resealed after a sample is acquired, as shown by microcartridge 112. Then, the microneedle cartridge is placed in receiver module 114 for analysis. Placing the cartridge into the receiver actuates two needles 116 and 118 that pierce the cartridge's seals. One needle injects sheath fluid into the cartridge while the other needle receives the sample and sheath fluid combined flow. The cartridge shown in FIG. 16 could simply be a sample taking component that passes the sample onto a reaction cartridge like those mentioned above or could contain reagents to process the sample internally.

Figure 18:
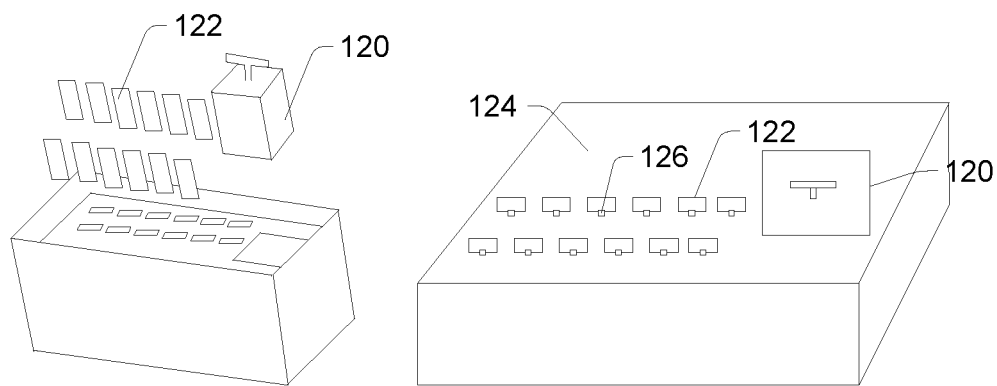
FIG. 18 is an isometric side view and a top view of a reagent storage module that may be included in the portable systems described herein.

It is often the case that reagents used in biological detection must be refrigerated or frozen when stored. The embodiments described herein, if used with such reagents, may include a refrigeration unit onboard portable system 12 for reagent storage module 4. One embodiment of a reagent storage module is shown in FIG. 18, which can store and refrigerate reagents and provide an interlock and indicator system so that used reagents are not accidentally used more than once. For example, as shown in FIG. 18, the reagent storage module may include detector reagent storage 120, which may have any suitable configuration known in the art. In FIG. 18, the reagent storage module is shown with cartridges 122 removed (on left) and with cartridges 122 inserted (on right). In addition, the reagent storage module may include indicator panel 124 that includes one or more indicators for each reaction cartridge. For example, the indicator panel may include indicator 126 for each reaction cartridge. The indicator may be changed depending on the status of the reagent cartridges in the reagent storage module. For example, a red light may indicate a used cartridge, an unlit indicator may indicate a missing reagent cartridge, and a green indicator may indicate a new reagent cartridge. Although the reagent storage module shown in FIG. 18 is configured for storing a particular number of reaction cartridges, it is to be understood that the reagent storage module may be configured to store any suitable number of reaction cartridges.

The embodiments described herein provide a number of advantages over other systems configured to perform measurements of samples. For example, the embodiments described herein are substantially insensitive to their environments. In addition, the embodiments described herein are not time consuming to manufacture. Additionally, the embodiments described herein are relatively simple to operate and can be used by relatively untrained users. Furthermore, the embodiments described herein are relatively inexpensive and are capable of performing the measurements without requiring significant laboratory resources for preprocessing of the one or more samples. Moreover, the embodiments described herein are relatively flexible in design such that a single system can be used for substantially different applications.

Further modifications and alternative embodiments of various aspects of the invention may be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A portable system for processing and analyzing biological or environmental samples, comprising:
   an automated assay preparation module configured to process a sample into a fluid assay with fluorescently tagged particles; and
   a microfluidic analysis module coupled to the automated assay preparation module, wherein the microfluidic analysis module comprises a chip-based flow cytometer having:
      a first input conduit for receiving the fluid assay;
      a second distinct conduit for receiving a sheath fluid;
      a fluid flow chamber coupled to the first and second input conduits, wherein the fluid flow chamber is configured to generate a fluid stream with the fluid assay confined within the sheath fluid;
      a channel coupled to the fluid flow chamber for routing the fluid stream through the flow cytometer;
      an illumination subsystem comprising a light source system and an optical system collectively configured to direct light toward an interrogation region of the channel;
      a measurement subsystem comprising:
         a collection system comprising collection optics configured to gather fluorescence emitted from the fluorescently tagged particles; and
         an examination system for analyzing the collected fluorescence;
      wherein the first conduit, second conduit, fluid flow chamber, channel, and at least some collection optics of the collection system are fixedly arranged within a substrate, and
      wherein the light source system is configured such that individual light sources within the light source system direct light at different spots within the interrogation region, and wherein the collection system is configured such that the fluorescent light emitted from the fluorescently tagged particles at each of the different spots is collected by a different detector of the collection system.

2. The portable system of claim 1, wherein the fluid flow chamber is configured to generate a fluid stream with the fluid assay having a first dimension of up to approximately 80 microns in a vertical direction perpendicular to the flow of the fluid stream and a second dimension of up to approximately 25 microns in a horizontal direction perpendicular to the flow of the fluid stream.

3. The portable system of claim 1, wherein the illumination subsystem is fixedly arranged relative to the substrate.

4. The portable system of claim 1, wherein the collection system comprises an aspherical mirror to direct light emitted from the fluorescently tagged particles to a detector of the collection system.

5. The portable system of claim 1, wherein the assay preparation module is configured to process a sample into a fluid assay with fluorescently tagged magnetic particles, and wherein the flow cytometer comprises a means for inducing a magnetic field along at least a portion of the channel such that the fluorescently tagged magnetic particles flow within a predetermined region of the fluid stream.

6. The portable system of claim 1, wherein the light source system is configured to direct light toward the interrogation region of the channel in a direction which is perpendicular to a direction from which the collection optics of the collection system are configured to gather fluorescence emitted from the fluorescently tagged particles.

7. The portable system of claim 1, wherein at least one of the individual light sources emits light within a different wavelength range than another of the individual light sources.

8. The portable system of claim 1, wherein the collection system comprises a different set of collection optics to direct the light emitted at each of the different spots to a different detector of the collection system.

9. The portable system of claim 1, wherein the substrate is configured to be not removable from the system.

10. A portable system for processing and analyzing biological or environmental samples, comprising:
   an automated assay preparation module configured to process a sample into a fluid assay with fluorescently tagged particles; and
   a microfluidic analysis module coupled to the automated assay preparation module, wherein the microfluidic analysis module comprises a chip-based flow cytometer having:
      a substrate configured to be non-removable with an embedded channel for routing the fluid assay through the flow cytometer;
      an illumination subsystem comprising a light source system and an optical system collectively configured to direct light toward an interrogation region of the channel; and
      a measurement subsystem comprising:
         a collection system comprising collection optics configured to gather fluorescence emitted from the fluorescently tagged particles; and
         an examination system coupled for analyzing the collected fluorescence, wherein the light source system is configured such that individual light sources within the light source system direct light at different spots within the interrogation region, and wherein the collection system is configured such that the fluorescent light emitted from the fluorescently tagged particles at each of the different spots is collected by a different detector of the collection system.

11. The portable system of claim 10, wherein the chip-based flow cytometer further comprises:
   a first input conduit for receiving the fluid assay;
   a second distinct conduit for receiving a sheath fluid; and
   a fluid flow chamber coupled to the first and second input conduits, wherein the fluid flow chamber is configured to generate a fluid stream having the fluid assay confined within the sheath fluid.

12. The portable system of claim 11, wherein the fluid flow chamber is configured to generate the fluid stream with the fluid assay having a first dimension of up to approximately 80 microns in a vertical direction perpendicular to the flow of the fluid stream and a second dimension of up to approximately 25 microns in a horizontal direction perpendicular to the flow of the fluid stream.

13. The portable system of claim 11, wherein the first conduit, second conduit, fluid flow chamber and at least some collection optics of the collection system are fixedly arranged upon or within the non-removable substrate.

14. The portable system of claim 10, wherein the illumination subsystem is fixedly arranged relative to the non-removable substrate.

15. The portable system of claim 10, wherein the collection system comprises an aspherical mirror to direct light emitted from the fluorescently tagged particles to a detector of the collection system.

16. The portable system of claim 10, wherein the assay preparation module is configured to process the sample into a fluid assay with fluorescently tagged magnetic particles, and wherein the flow cytometer comprises a means for inducing a magnetic field along at least a portion of the channel such that the fluorescently tagged magnetic particles flow within a predetermined region of the fluid assay.

17. The portable system of claim 10, wherein the light source system is configured to direct light toward the interrogation region of the channel in a direction which is perpendicular to a direction from which the collection optics of the collection system are configured to gather fluorescence emitted from the fluorescently tagged particles.

18. The portable system of claim 10, wherein at least one of the individual light sources emits light within a different wavelength range than another of the individual light sources.

19. The portable system of claim 10, wherein the collection system comprises a different set of collection optics to direct the light emitted at each of the different spots to a different detector of the collection system.

* * * * *